United States Patent [19]

Mellor

[11] Patent Number: 4,615,221
[45] Date of Patent: Oct. 7, 1986

[54] TRIAXIAL COMPRESSION TEST APPARATUS

[75] Inventor: Malcolm Mellor, Hanover, N.H.

[73] Assignee: The United States of America as represented by the Secretary of the Army, Washington, D.C.

[21] Appl. No.: 751,395

[22] Filed: Jul. 3, 1985

[51] Int. Cl.[4] ............................................. G01N 3/00
[52] U.S. Cl. ........................................................ 73/798
[58] Field of Search .................. 73/798, 819, 825, 807, 73/816, 840

[56] References Cited

U.S. PATENT DOCUMENTS

| | | |
|---|---|---|
| 3,035,437 | 5/1962 | Watkins et al. . |
| 3,505,860 | 4/1970 | Bishop et al. . |
| 3,616,685 | 11/1971 | Strom ........................................ 73/84 |
| 3,728,895 | 4/1973 | Shaw . |
| 3,797,303 | 3/1974 | Bascoul et al. . |
| 3,820,385 | 6/1974 | Cordoba ................................... 73/84 |
| 3,975,950 | 8/1976 | Erdel . |
| 4,332,175 | 6/1982 | Krainski, Jr. ........................... 73/825 |

FOREIGN PATENT DOCUMENTS 276476 10/1970 U.S.S.R. .................................. 73/807

OTHER PUBLICATIONS

Ignat'ev, L. N. et al., Accelerated-Test System . . . States, from Ind. Lab. (USA), vol. 44, No. 1, Jan. 1978, pp. 149, 150.

Primary Examiner—Jerry W. Myracle
Attorney, Agent, or Firm—Charles W. Calkins

[57] ABSTRACT

A triaxial compression test apparatus includes a cylindrically-shaped sample disposed in a fixed-hydraulic cylinder with the sample's ends disposed between a first piston and the fixed cylinder's base. An annular space for hydraulic fluid surrounds the remaining surface of the sample. The first piston, located in the fixed cylinder, includes a rod mechanically coupled to the housing of a floating hydraulic cylinder housing a second piston therein. A single force applied to the second piston, 1. transmits a first force, via the first piston, along the longitudinal axis of the sample and 2. transmits a second force along the axial axes of the sample via a hydraulic fluid coupled from the floating cylinder to the annular space of the fixed cylinder. A constant ratio is maintained between the two forces.

18 Claims, 1 Drawing Figure

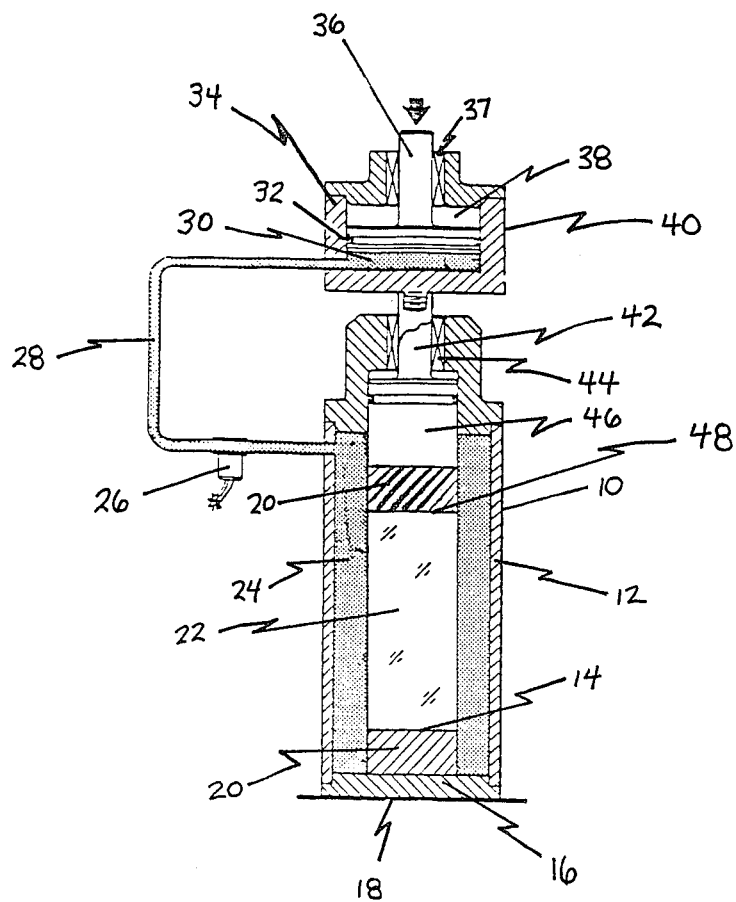

TRIAXIAL COMPRESSION TEST APPARATUS

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

1. Field of the Invention

The invention relates generally to an apparatus for testing geological and other naturally occuring and fabricated samples to determine their mechanical properties. The invention particularly relates to an apparatus for conducting constant-strain-rate triaxial tests. The apparatus is designed so that the confining pressure/axial stress ratio remains constant.

2. Description of the Prior Art

A testing apparatus is known wherein a self-supporting sample is subjected to external forces in a tri-axial cell. The term sample is used to describe both geological samples and other naturally occuring and fabricated articles. A tri-axial cell typically comprises a pressure chamber, in which the sample can be located, a means for applying a force to the sample, and a means for measuring the force applied to the sample. With such an apparatus various characteristics of the sample under test, such as its compressive and shear strengths, can be determined.

U.S. Pat. No. 3,505,860, Bishop, et. al, discloses a geological sample testing apparatus having a cylinder containing the sample, and a piston and a hydraulic fluid as means for applying forces to the sample. In utilizing the apparatus in Bishop, two forces are applied to the cylinder having the sample disposed therein. The first force is applied to the hydraulic fluid through the base of the cylinder and is coupled to apply force to the axial axes of the sample. The second force is applied mechanically via the piston to the longitudinal axis of the sample. The axial movement of the piston, under various loads, correlates to the structural properties of the sample.

SUMMARY OF THE INVENTION

According to the present invention, a single force, applied to a second piston, is coupled to the first piston to apply a force to the longitudinal axis of the sample and coupled to an hydraulic fluid to apply force to the axial axes of the sample. The confining force the hydraulic fluid exerts along the axial axes of the sample is not maintained at a predetermined constant value. The force exterted by the hydraulic fluid along the axial axes of the sample is ramped in constant proportion to the force applied to the longitudinal axis of the sample by the first piston. The ratio of the force applied by the first piston to the force applied by the hydraulic fluid can be varied in the present invention by changing the diameter of the first piston. The ability to change the ratio allows for a more accurate testing of the sample.

According to the present invention a testing apparatus comprises a first enclosure within which a sample may be placed, a hydraulic fluid and a first piston in communication with the sample, a second enclosure, containing hydraulic fluid in communication with the hydraulic fluid in the first enclosure, attached to the piston rod of the first piston, having a second piston which simultaneously transfers a force to the hydraulic fluid surrounding the sample and the first piston. A force applied to the second piston is coupled to the first piston to apply a force along the longitudinal axis of the sample, and the hydraulic fluid to apply a force along the axial axes of the sample. The ratio between these axial forces remains constant throughout the testing of the sample.

The present invention may be carried into practice in a number of ways. One specific embodiment will be described with reference to the accompanying figure.

The apparatus includes a fixed enclosure 10 having a base 16, secured to a substrate 18, and a side wall 12. Enclosure 10, as shown in the figure, is cylindrically shaped, however other shapes may be used. A sample 22, to be tested, is shown inside enclosure 10 defining a hydraulic fluid cavity 24 between the side 12 of enclosure 10 and sample 22. End 14 of the sample is in contact with the base 10 and the opposite end 48 is in contact with a piston 46. In order to prevent contamination of the sample, caps 20 may be used on the ends of the sample 22 to avoid direct contact between the sample 22 and the base 16 or the piston 46. A piston rod 42 attached to the piston 46 extends upward from enclosure 10. A bearing material 44 is used to reduce friction between the piston rod 42 and enclosure 10 as piston rod 42 moves in or out of enclosure 10. The piston rod 42 is mechanically attached to a floating enclosure 40. One such means of attaching consists of a male threaded portion of enclosure 40 attached to a female threaded receptacle in the piston rod 42. Enclosure 40, as shown in the figure, is cylindrically shaped, however other shapes may be used. Enclosure 40 contains a piston 38, having a rod 36 which extends upwards from enclosure 40. Bearing material 37 is used to reduce friction between the piston rod 36 and enclosure 40 as piston rod 36 moves in or out of enclosure 40. Piston 38 as mounted in enclosure 40 defines a cavity 30 between piston 38 and the side 34 of enclosure 40 containing hydraulic fluid. A seal 32 is used between piston 38 and the side 34 of enclosure 40. The hydraulic fluid in cavity 30 communicates with the hydraulic fluid in cavity 24 via conduit 28. A hydraulic fluid pressure gauge 26 is coupled to conduit 28 for measuring the hydraulic fluid pressure in conduit 28.

In using the apparatus to perform tests, a suitably prepared sample 22, alternatively with protective end caps 20, is placed in enclosure 10. End 14 of the sample rests against the base 16 of enclosure 10, and end 48 of the sample is in contact with piston 46. Hydraulic fluid is allowed to fill cavity 24, conduit 28, and cavity 30, thereby surrounding sample with hydraulic fluid. A single force applied to piston 38, as indicated by the arrow in the drawing, is coupled to the hydraulic fluid in chamber 30 thereby simultaneously resulting in a force being applied along the axial axes of sample 22 by fluid surrounding sample 22 within cavity 42 and resulting in a force being applied along the longitudinal axis of sample 22 by piston 46. The force exerted on the hydraulic fluid in cavity 30 is mechanically coupled to piston 46 through enclosure 40 for application along the longitudinal axis of sample 22. The ratio between the force transmitted by piston 46 and the force transmitted by the hydraulic fluid will remain constant as additional force is applied to piston rod 36.

The apparatus described can be utilized to determine certain physical characteristics of the sample by relating the force applied to the longitudinal axis of the sample, which can be determined by the extent of the axial movement of piston 46, and the force applied to the axial axes of the sample, which can be determined by use of the pressure measuring means 26.

While one specific embodiment of the present invention has been described, the invention is not limited to this particular form, but rather is applicable to all such variations which fall within the scope of the following claims.

What I claim is:

1. An apparatus comprising:
   a sample;
   an enclosure, containing said sample
   a means for generating a force;
   a means for simultaneously coupling said force to a first and second portion of said sample, said means comprising a mechanical means for coupling said force to said first portion of said sample, and a hydraulic means communicating with said mechanical means, for coupling said force to said second portion of said sample, wherein said mechanical means comprise a first piston communicating with said sample and means for coupling said force to said first piston whereby said coupling means comprise a second enclosure, with a second piston, having a rod, forming a chamber within said second enclosure containing a hydraulic fluid, whereby said force being applied to said second piston rod is transmitted to said hydraulic fluid and thereby coupled to said second enclosure and a means for communicating said force form said second enclosure to said first piston.

2. The apparatus as recited in cliam 1 wherein said communicating means between said second enclosure and said first piston further comprise:
   a mechanical means of connecting said second enclosure to said first piston thereby coupling said force coupled to said second enclosure to said second piston.

3. The apparatus as recited in claim 2 wherein said communicating means between said second enclosure and said first piston further comprise:
   a first piston rod, having threads on an end opposite said first piston said threads being mechanically attached to a threaded portion of said second enclosure.

4. The apparatus as recited in claim 1 wherein said hydraulic means further comprise:
   said hydraulic fluid encircling said sample, in an annular space defined between said sample and said enclosure; and means for coupling said force to said hydraulic fluid.

5. The apparatus as recited in claim 1 further comprising:
   a means for coupling said hydraulic fluid from said second enclosure to said sample containing enclosure, said hydraulic fluid thereby transmitting said force applied to said hydraulic fluid to said second portion of said sample.

6. The apparatus as recited in claim 1 wherein said first portion of said sample comprises a longitudinal axis and said second portion of said sample comprises two axes perpendicular to said longitudinal axis.

7. The apparatus as recited in claim 6 wherein said force coupling means further comprise:
   a mechanical means for coupling said force to said longitudinal axis of sample; and
   a hydraulic means, communicating with said mechanical means, for coupling said force to said two axes of said sample.

8. The apparatus as recited in claim 7 wherein said mechanical means further comprise:
   a first piston communicating with said sample; and
   means for coupling said force to said first piston.

9. The apparatus as recited in claim 8 wherein said means for coupling said force to said first piston further comprise:
   a second enclosure;
   a second piston, having a rod , forming a chamber within said second enclosure containing a hydraulic fluid, whereby said force being applied to said second piston rod is transmitted to said hydraulic fluid and thereby coupled to said second enclosure; and
   a means for communicating said force from said second enclosure to said first piston.

10. The apparatus as recited in claim 9 wherein said communicating means between said second enclosure and said first piston further comprise:
    a mechanical means of connecting said second enclosure to said first piston thereby coupling said force coupled to said second enclosure to said second piston.

11. The apparatus as recited in claim 10 wherein said communicating means between said second enclosure and said first piston further comprise:
    a first piston rod, attached to said first piston, having threads on a end opposite said first piston, said threads being mechanically attached to an threaded portion of said second enclosure.

12. The apparatus as recited in claim 7 wherein said hydraulic means further comprise:
    a hydraulic fluid encircling said sample, said hydraulic fluid in an annular space defined between said sample and said first enclosure; and means for coupling said force to said hydraulic fluid.

13. The apparatus as recited in claim 12 wherein said means for coupling said force to said hydraulic fluid further comprise:
    a second enclosure; and
    a second piston, having a rod, forming a chamber within said second enclosure containing a hydraulic fluid, whereby said force being applied to said second piston rod is transmitted to said hydraulic fluid.

14. The apparatus as recited in claim 13 further comprising:
    a means for coupling said hydraulic fluid from said second enclosure to said sample containing first enclosure, said hydraulic fluid thereby transmitting said force applied to said hydraulic fluid to said two axes of said sample.

15. The apparatus as recited in claim 1 further comprising:
    a means for measuring the pressure of said hydraulic fluid.

16. An apparatus comprising:
    a sample;
    a fixed enclosure containing said sample, said sample and said enclosure defining an annular space therebetween containing a hydraulic fluid;
    a first piston for coupling a force to said sample;
    a floating enclosure mechanically coupled to said first piston;

a second piston located in said floating enclosure, said second piston and said floating enclosure defining a space for said hydraulic fluid, said space communicating with said annular space; and a means for coupling said force to said second piston wherein said force is coupled to said hydraulic fluid in said floating enclosure and then to said sample through said hydraulic fluid in said annular space and to said sample through said first piston.

17. An apparatus comprising:

an elongated sample;

a first cylindrical enclosure, containing said sample, having an annular space defined between said sample and said walls of said first enclosure for a hydraulic fluid, said hydraulic fluid thereby encircling said sample;

a first piston located in said first enclosure, having a first piston rod, extending from said first enclosure, said first piston communicating with said sample along a first portion of said sample; a second cylindrical enclosure, mechanically attached to said first piston rod;

a means for said hydraulic fluid to communicate between said first enclosure and said second enclosure;

a second piston located in said second enclosure, having a second piston rod extending from said second enclosure, said second piston defining a chamber between said second piston and said second enclosure for said hydraulic fluid;

a means for applying a force to said second piston rod, said force coupled to said hydraulic fluid and through said hydraulic fluid to said second enclosure, thereby coupling said force to said first piston and thereby to said first portion of said sample, and to said hydraulic fluid in said first enclosure and thereby to said second portion of said sample; and a means for measuring the pressure of said hydraulic fluid.

18. An apparatus comprising:

an elongated sample having a longitudinal axis and two axes perpendicular thereto;

a first cylindrical enclosure, containing said sample, having an annular space defined between said sample and said walls of said first enclosure for a hydraulic fluid, said hydraulic fluid thereby communicating with said two axes of said sample;

a first piston located in said first enclosure, having a first piston rod, extending from said first enclosure, said first piston communicating with said sample along said longitudinal axis of said sample; a second cylindrical enclosure, mechanically attached to said first piston rod;

a means for said hydraulic fluid to communicate between said first enclosure and said second enclosure;

a second piston located in said second enclosure, having a second piston rod extending from said second enclosure, said second piston defining a chamber between said second piston and said second enclosure for said hydraulic fluid;

a means for applying a force to said second piston rod, said force coupled to said hydraulic fluid and through said hydraulic fluid to said second enclosure, thereby coupling said force to said first piston and thereby to said longitudinal axis of said sample, and to said hydraulic fluid in said first enclosure and thereby to said two axes of said sample; and a means for measuring the pressure of said hydraulic fluid.

* * * * *